United States Patent [19]

Muller

[11] 4,161,615

[45] Jul. 17, 1979

[54] DEHYDROGENATION OF CYCLIC KETONES TO BETA-NAPHTHOLS

[75] Inventor: Werner H. Müller, Kelkheim, Fed. Rep. of Germany

[73] Assignee: Hoechst Aktiengesellschaft, Frankfurt am Main, Fed. Rep. of Germany

[21] Appl. No.: 800,915

[22] Filed: May 26, 1977

Related U.S. Application Data

[63] Continuation of Ser. No. 649,496, Jan. 15, 1976, abandoned.

[30] Foreign Application Priority Data

Jan. 17, 1975 [DE] Fed. Rep. of Germany ....... 2501770

[51] Int. Cl.² .......................................... C07C 39/14
[52] U.S. Cl. .................................................. 568/740
[58] Field of Search ..................... 260/621 H; 568/740

[56] References Cited

U.S. PATENT DOCUMENTS

| 2,291,585 | 7/1942  | Barlett et al. ................... 260/621 H |
| 2,503,641 | 4/1950  | Taylor et al. ................... 260/621 H |
| 3,345,382 | 10/1967 | Kremer ............................ 260/621 H |
| 3,534,110 | 10/1970 | Juguin et al. ................... 260/621 H |
| 4,024,196 | 5/1977  | Krekeler et al. ................ 260/621 H |

FOREIGN PATENT DOCUMENTS

1144731 3/1963 Fed. Rep. of Germany ...... 260/621 H

*Primary Examiner*—Joseph E. Evans
*Attorney, Agent, or Firm*—Curtis, Morris & Safford

[57] ABSTRACT

Preparation of 2-hydroxynaphthalenes optionally substituted by aliphatic or aromatic radicals from cycloalkenones or hydroxycycloalkanones by heating them in the presence of a dehydrogenation agent.

1 Claim, No Drawings

DEHYDROGENATION OF CYCLIC KETONES TO BETA-NAPHTHOLS

This is a continuation of application Ser. No. 649,496 filed Jan. 15, 1976, now abandoned.

The present invention provides a novel process for the preparation of 2-hydroxynaphthalenes by dehydrogenation of the reaction products obtained from cyclohexanones and α, β-unsaturated ketones in the Robinson anellation.

Hitherto, the industrial-scale manufacture of 2-hydroxynaphthalenes consists in reacting naphthalenes with sulfuric acid, neutralizing the naphthalenesulfonic acid, fusing the naphthalene sulfonate with caustic soda, and liberating the hydroxynaphthalene by means of sulfuric acid. The disadvantage of this process resides in the fact that large amounts of salts ($Na_2SO_3$, $Na_2SO_4$) are inevitably formed which have to be removed from the sewage water with great expenditure.

Furthermore, it is known to obtain 2-hydroxynaphthalene by catalytic dehydrogenation of β-tetralone. However, this process yields only 26% of β-naphthol, apart from 54% of naphthalene.

2-hydroxynaphthalenes are important intermediate products for organic dyestuffs.

There has now been found a process for the preparation of 2-hydroxy-naphthalenes of the formula

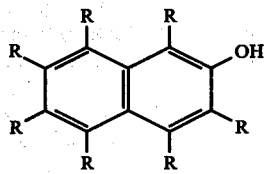

wherein the radicals R, being identical or different, are hydrogen, aliphatic or aromatic radicals; adjacent aliphatic radicals R optionally forming together an alicyclic 5- or 6-membered ring, which comprises heating cycloalkenones or hydroxycycloalkanones of the formulae II to IV

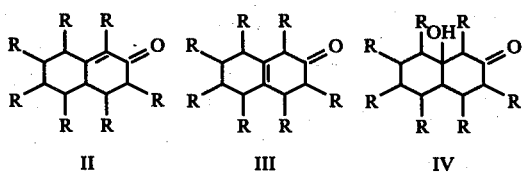

wherein the radicals R are as defined above, in the presence of a dehydrogenating agent.

The compound of formulae II, III and IV may be obtained in known manner, for example from α,β-unsaturated ketones and cyclic ketones such as cyclohexanones, or α- and β-decalones or their enamines or ketimines.

Suitable aliphatic radicals are straight-chain, branched or cyclic alkyl radicals, preferably those having up to 12 carbon atoms. Especially methyl, ethyl, propyl, butyl, pentyl, hexyl, octyl, decyl, dodecyl, cyclopentyl, cyclohexyl and cyclododecyl are preferred.

Generally, the radicals R together do not contain more than 24 carbon atoms. The alkyl radicals may be substituted, for example by halogen, especially fluorine or chlorine, or by phenyl, naphthyl, hydroxy, methoxy, acetoxy, carbamide or carbonitrile, but also by carbalkoxy having up to 6 carbon atoms, for example carboxymethyl (—$COOCH_3$) or carboxyethyl (—$COOC_2H_5$).

Suitable aromatic radicals are for example aryl groups having from 6 to 14 carbon atoms; phenyl or naphthyl being preferred. The aryl groups may be substituted, for example by halogen, especially fluorine or chlorine, alkyl having up to 6 carbon atoms, or by trifluoromethyl or nitro, but also by alkoxy having up to 6 carbon atoms such as methoxy or ethoxy.

Dehydrogenation of the cycloalkenones or hydroxyalkanones is carried out by heating them in the presence of a dehydrogenating agent, for example by reaction with sulfur, selenium, chloranil, Pd(II) salt, or by heating them in the presence of a dehydrogenation catalyst.

Suitable dehydrogenation catalysts are for example ruthenium, rhodium, palladium, osmium, iridium and platinum, but also metals such as copper, silver, gold, iron, cobalt, nickel and chromium, or mitures of these elements, as well as also the salts thereof. Suitable salts are for example chlorides, oxides, acetates or carbonates. Preferred elements are palladium, platinum, ruthenium and copper, or the salts thereof.

The catalysts are preferably used on carriers, for example on carbon, aluminum oxide, silicic acid, magnesium oxide, calcium oxide, titanium oxide and asbestos, or a mixture of two or more of the cited carriers. Palladium on carbon is especially recommended. The concentration of the catalyst is advantageously from 0.02 to 20 weight %, relative to the carrier, preferably from 0.1 to 10 weight %.

The process may be carried out in the liquid or gaseous phase, batchwise or continuously.

Operations in the liquid phase are generally carried out at temperatures of from 140° to 350° C. and under a pressure sufficient for maintaining the liquid phase. Temperatures of from 180° to 250° C. are preferred, since these temperatures ensure an especially high selectivity and simultaneously a very rapid course of the dehydrogenation reaction.

The reaction pressure in the case of liquid phase operation is generally from 0.5 to 20 atmospheres, but it must be at least sufficient for maintaining a liquid phase.

It is important to keep low the partial pressure of the hydrogen formed during the dehydrogenation, so that the equilibrium is shifted in favor of the dehydrogenation and hydrogenation or hydrogenolysis of the starting compounds and final products is prevented. Such a low hydrogen partial pressure may be obtained by flushing the reaction system with an inert gas, for example nitrogen or carbon dioxide.

Liquid phase operation may be carried out in the presence of a suitable solvent, for example aliphatic ethers, aromatic ethers, such as diphenyl ether; hydrocarbons, such as benzene, toluene, xylene, pseudocumene, naphthalene, biphenyl, tetraline, decaline; ketones, such as acetone, diethylketone, methylethylketone or methylisobutylketone; esters, such as cyclohexyl propionate or trimethyleneglycol diacetate; but also acid amides, for example dimethyl formamide or N-methyl-pyrrolidone, alcohols, phenols, water or the reaction product itself are suitable.

Preferred solvents are aliphatic ethers, for example polyglycol dialkyl ethers, such as di- tri- or tetraethyleneglycol dialkyl ethers having generally alkyl groups of up to 6 carbon atoms.

Especially advantages are polyglycol dimethyl and di-ethyl ethers. The polyglycol dialkyl ethers have the advantage of boiling under atmospheric pressure in the preferred temperature range of from 180° to 260° C., which is extremely favorable for the process of the invention, since it allows operating without pressure and since the dehydrogenation with reflux in the preferred temperature range proceeds most rapidly and with high selectivity.

The efficiency of the process is increased by vigorous agitation of the reaction mixture as long as it is in contact with the catalyst.

It is very advantageous to operate in the presence of hydrogen accepting substances, that is, substances which bind the hydrogen immediately after its formation, thus ensuring that the dehydrogenation reaction proceeds under relatively gentle conditions. Suitable hydrogen acceptors are unsaturated compounds such as styrene, $\alpha$- and $\beta$-methylstyrene, stilbene, anthracene, acenaphthylene, crotonic acid, maleic acid, fumaric and cinnamic acid as well as the alkyl esters of these acids with alcohols having up to 6 carbon atoms, butene-diol, butinediol and their acetates and propionates, mesityl oxide, benzalacetone or maleic acid anhydride. Also nitro compounds, for example nitrobenzene, p-nitrotoluene or o-nitrophenol are appropriate.

The process of the invention is generally carried out in the presence of a fixed bed catalyst or a catalyst being maintained in suspension in the reaction solution by vigorous agitation.

In the case of using a fixed bed catalyst, the particle size of the catalyst is advantageously from 0.5 to 10 mm, preferably from 2 to 5 mm.

In the case where a catalyst on a carrier suspended in the reaction medium is used, a particle size of the catalyst of from 0.01 to 5 mm, preferably from 0.05 to 1 mm, is recommended. Depending on the nature of the liqud and the catalyst, the suspension contains generally from 0.1 to 40 parts by weight of catalyst on carrier per 100 parts by weight of the liquid. A ratio of from 1 to 30 parts by weight of catalyst on carrier per 100 parts by weight of solvent is preferred.

When the process is carried out in the gaseous phase, a carrier gas such as nitrogen, $CO_2$, or hydrogen or a hydrogen acceptor such as ethylene or propylene, or highly volatile solvents, for example alcohols, ethers, acetic acid or acetone, may be added to the starting material before the vaporization. Water is most advantageous, since its presence increases considerably the selectivity of 2-hydroxy-napthalene formation, because it prevents formation of naphthalene.

In the liquid as well as in the gaseous phase, the temperature and the residence time necessary for dehydrogenation may vary within a wide range, depending on the starting materials and the kind of catalyst used. Generally, operations are carried out at temperatures of from 160° to 450° C., preferably from 200° to 350° C., continuously or batchwise, under reduced or normal pressure, although higher pressures are allowed, for example 20 atmospheres, on condition that the $H_2$ partial pressure is kept low.

The following examples illustrate the invention.

EXAMPLES

The starting materials for Examples 1 to 5 have been prepared according to the method described in Organic Syntheses, Vol. 45, pp. 80–83, and identified according to the data indicated by R. L. Augustine, et al. in Chem. Ind. (London), 1963, pp. 490/491.

EXAMPLE 1

In a three-necked flask having a capacity of 100 ml and provided with thermometer, reflux condenser and gas collector vessel, 50 ml of diethyleneglycol diethyl ether, 1 g of dehydrogenation catalyst (0.1 g Pd on 0.9 g active carbon and 4.8 g (0.032 mol) of a mixture composed of about 80% of $\Delta^{1\,(9)}$-octalone-2, 10% of $\Delta^{9\,(10)}$-octalone-2 and 10% of 9-hydroxydecalone-2 were heated for 5 hours at 190° C., which caused the development of 2.1 l of gas. After suction-filtration of the catalyst, the gas chromatography analysis of the filtrate yielded 3.9 g of $\beta$-naphthol (85 mol %) and 0.5 g of naphthalene (12 mol %).

EXAMPLE 2

4.8 g of the oxo-cycloaliphatic mixture of Example 1 and 1 g of Pd/C catalyst (0.1 g Pd, 0.9 g active carbon) were heated for 1 hour at 215°–220° C., which caused the development of 2.0 l of gas. After cooling, the reaction mixture was digested with 30 ml of di-ethyleneglycol diethyl ether, and the catalyst was suction filtered. The gas chromatography analysis of the filtrate yielded 3.2 g of $\beta$-naphthol (70% of the theoretical yield) and 0.9 g of naphthalene (22% of the theoretical yield).

EXAMPLE 3

In a glass reactor having a diameter of 10 mm and a length of 120 mm, there were 5 ml of catalyst (2.0 weight % of Pd on active carbon; bulk density 0.5 g/ml, diameter 0.2–2 mm). The catalyst temperature was maintained during the reaction at 320° C. by means of an electric stove. Before the reaction, the catalyst had been activated for 2 hours at 170° C. by means of 0.7 l/h of $N_2$ and 1.4 l/h of $H_2$.

Subsequently, 2.25 g/h of the oxocycloaliphatic mixture described in Example 1, 0.7 l of $N_2$ and 1.4 l of $H_2$ per hour were fed via an evaporator preheated to 350° C. to the above catalyst having a temperature of 320° C. The product collected at the reactor outlet in a cooled collector vessel solidified in the form of white crystals (2.15 g/h) having a melting point of 106° C., which crystals, according to GLC analysis, consisted of 60% of $\beta$-naphthol and 35% of naphthalene.

EXAMPLE 4

The glass reactor described in Example 3 was charged with the catalyst described in the same Example.

After a 2 hour activation by means of 0.7 l/h of $N_2$ and 1.4 l/h of $H_2$ at 170° C., 1.9 g/h of the oxo-cycloaliphatic mixture as described in Example 1, and 1.4 l of $H_2$, 2.0 g of $H_2O$ and 0.7 l of $N_2$ (all per hour) were fed to the catalyst having a temperature of 285° C. The product obtained in the cooled collector vessel was in the form of an aqueous crystal pulp which, according to GLC analysis, contained 1.5 g (82% of the theoretical yield) of $\beta$-naphthol and 0.24 g (15% of the theoretical yield) of naphthalene.

EXAMPLE 5

0.5 g of 9-hydroxydecalone-2 (melting point 145° C.) and 0.1 g of catalyst (0.01 g of Pd on 0.09 g of active carbon) were heated for 20 minutes at 210° C. in an Erlenmeyer flask having a capacity of 20 ml whereby gas development occurred. After cooling, 10 ml, of ethanol were added, the catalyst was separated by filtration, and the filtrate was subjected to thin layer chromatography on silica gel plates with an ether/hexane 1/1 mixture as solvent, whereby β-naphthol was detected. On spraying with a methanolic solution of fast blue salt BB and subsequent treating with ammonia vapor, β-naphthol was indicated as a violet spot having a $R_f$ value of 0.51. Color and $R_f$ value are identical to color and $R_f$ value of genuine β-naphthol.

What is claimed is:

1. A process for the preparation of 2-hydroxy-naphthalenes of the formula

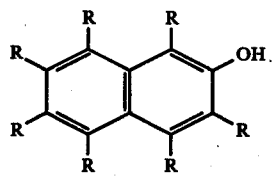

wherein the radicals R are selected from:
(a) hydrogen,
(b) straight chain, branched chain and cyclic alkyl radicals and
(c) phenyl and naphthyl, and adjacent aliphatic radicals R may together form an alicyclic 5- or 6-membered ring, and the R substituents taken together do not contain more than 24 carbon atoms, which comprises heating a cycloalkenone or hydroxycycloalkanone of the formulae II to IV

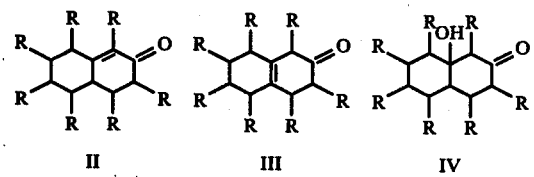

wherein the radicals R are as defined above, in the liquid phase at a temperature of 140° to 350° C. and a pressure of up to 20 atmospheres in a solvent which is a polyglycol dialkyl ether having alkyl groups of up to 6 carbon atoms and a noble metal catalyst of the 8th subgroup of the Periodic System.

* * * * *